(12) United States Patent
Zhao et al.

(10) Patent No.: US 11,737,662 B2
(45) Date of Patent: Aug. 29, 2023

(54) VISUAL IMAGING DEVICE BASED ON PS-OCT FOR EARLY DEMINERALIZATION AND CARIES OF DENTAL HARD TISSUES

(71) Applicant: XUANWU HOSPITAL, CAPITAL MEDICAL UNIVERSITY, Beijing (CN)

(72) Inventors: Ying Zhao, Beijing (CN); Yuhao Bai, Beijing (CN)

(73) Assignee: XUANWU HOSPITAL, CAPITAL MEDICAL UNIVERSITY, Beijing (CN)

( * ) Notice: Subject to any disclaimer, the term of this patent is extended or adjusted under 35 U.S.C. 154(b) by 266 days.

(21) Appl. No.: 17/186,162

(22) Filed: Feb. 26, 2021

(65) Prior Publication Data
US 2021/0338084 A1 Nov. 4, 2021

(30) Foreign Application Priority Data
Apr. 29, 2020 (CN) .......................... 202010357732.1

(51) Int. Cl.
*A61B 1/247* (2006.01)
*A61B 1/05* (2006.01)
(Continued)

(52) U.S. Cl.
CPC .......... *A61B 1/247* (2013.01); *A61B 1/00009* (2013.01); *A61B 1/00042* (2022.02);
(Continued)

(58) Field of Classification Search
CPC . A61B 1/247; A61B 1/00009; A61B 1/00042; A61B 1/00194; A61B 1/051;
(Continued)

(56) References Cited

U.S. PATENT DOCUMENTS

| 7,965,392 B2 * | 6/2011 | Tamura | A61B 5/0066 356/497 |
| 2005/0283058 A1 * | 12/2005 | Choo-Smith | A61B 5/0088 356/73 |

(Continued)

*Primary Examiner* — Tarifur R Chowdhury
*Assistant Examiner* — Carlos Perez-Guzman
(74) *Attorney, Agent, or Firm* — Woods Oviatt Gilman LLP; Katherine H. McGuire, Esq.

(57) ABSTRACT

Disclosed is a visual imaging device based on PS-OCT for early demineralization and caries of dental hard tissues, comprising a laser light source for emitting a laser light, a coupler for receiving and dividing the laser light emitted by the laser light source into a reference laser light and a detection laser light; wherein the reference laser light back-tracking to the coupler and the detection laser light back-tracking to the coupler are coupled and then passed through a transmission grating and a convex lens to input as an optical signal into a linear CCD detector for converting the optical signal into an electrical signal which is then input to a computer control system and collected by a built-in capture card; and the computer is configured to perform a three-dimensional reconstruction of an image and perform two-dimensional cross-section image analysis; and the computer control system is connected to the scanning galvanometer to control a vibration of the scanning galvanometer. The device of the present application can be used for performing PS-OCT imaging detection of the dental hard tissue surface in the oral cavity of a subject. The computer control system automatically performs two-dimensional cross-section imaging and three-dimensional reconstruction imaging of the image, thereby completing a three-dimensional quantitative evaluation. The present application provides a new method for clinically detecting early demineralization of dental hard tissue with high resolution.

1 Claim, 3 Drawing Sheets

(51) Int. Cl.
*A61B 5/00* (2006.01)
*A61B 1/00* (2006.01)

(52) U.S. Cl.
CPC .......... *A61B 1/00194* (2022.02); *A61B 1/051* (2013.01); *A61B 5/0066* (2013.01); *A61B 5/0088* (2013.01); *A61B 5/742* (2013.01); *A61B 5/7475* (2013.01)

(58) Field of Classification Search
CPC ............ A61B 1/00117; A61B 1/00172; A61B 1/00177; A61B 1/042; A61B 1/045; A61B 1/0615; A61B 5/0066; A61B 5/0088; A61B 5/742; A61B 5/7475; A61B 5/4547; G06T 11/003; G06T 17/00; G06T 2210/41
See application file for complete search history.

(56) References Cited

U.S. PATENT DOCUMENTS

| | | | | |
|---|---|---|---|---|
| 2009/0061381 | A1* | 3/2009 | Durbin | A61C 13/0004 433/213 |
| 2014/0078510 | A1* | 3/2014 | Rubio Guivernau | G01B 9/02064 356/479 |
| 2014/0115022 | A1* | 4/2014 | Yasuno | G01B 9/02088 708/204 |
| 2018/0049642 | A1* | 2/2018 | Mak | A61B 90/37 |

* cited by examiner

VISUAL IMAGING DEVICE BASED ON PS-OCT FOR EARLY DEMINERALIZATION AND CARIES OF DENTAL HARD TISSUES

CROSS REFERENCE TO RELATED APPLICATION

This application claims the benefit of Chinese Patent Application No. 202010357732.1, filed on Apr. 29, 2020, the entire disclosure of which is incorporated herein by reference in its entirety for all intended purposes.

TECHNICAL FIELD

The present application relates to the field of medical equipment, and in particular to a visual imaging device based on Polarization Sensitive-Optical Coherence Tomography (PS-OCT) for early demineralization and caries of dental hard tissues and a method of use thereof.

BACKGROUND

Optical Coherence Tomography (OCT) is an optical imaging technology that has developed rapidly in the past ten years. The technology involves use of the basic principles of weak coherence light interferometers for detecting signals of back reflections or several scatterings of incident weak coherent light at different depth levels of biological tissues, and obtaining two-dimensional or three-dimensional images of biological tissues through scanning. The OCT technology has developed rapidly in recent years, and has become another new type of biological tissue imaging technology following ultrasound technology, X-ray computed tomography (XCT), and magnetic resonance imaging (MRI). The OCT technology which integrates confocal microscopy technology and ultra-sensitive detection technology, combined with automatic control and computer graphics imaging processing technology, can realize non-destructive and radiation-free detection of human biological tissues, and finally obtain high-resolution tomographic images of the internal microstructure of the biological tissue in the body.

Polarization Sensitive Optical Coherence Tomography (PS-OCT) is an improved OCT system that involves use of polarized incident lights. The incident light of the orthogonal polarization can reduce the strong reflection by the enamel surface, and at the same time depolarize the scattering, thereby increasing the reflection by the demineralized enamel under the surface layer. Therefore, the demineralization degree can be quantified by directly using the orthogonal polarization reflectance regardless of the tooth surface morphology. Therefore, PS-OCT is especially suitable for the detection of enamel demineralization.

Caries is a common and frequently-occurring disease of the oral cavity, and is a chronic infectious disease of the dental hard tissue caused by bacteria. If caries are not effectively treated, it would cause the destruction of the dental hard tissues, further develop into pulpal and periapical diseases, even cause inflammations of the jaw, and eventually lead to tooth loss. Caries are characterized by a high incidence and a wide range of populations, and are one of the most common diseases in human beings. The World Health Organization (WHO) has listed caries, tumors and cardiovascular diseases as the three major diseases needed to be prevented and treated, and untreated dental caries is the most prevalent of all the 219 conditions included in the Global Burdan of Disease Study.

Caries usually manifests as demineralization of dental hard tissues in the early stage. The demineralization that occurs on smooth enamel surfaces (such as buccal labial surfaces) is often manifested as white spots or plaques without substantial tooth defects. However, early carious demineralization that occurs in the pit and fissure area of the tooth or the adjacent area of the tooth is difficult to detect with naked eyes. The undermining development of caries in these parts often leads to the fact that when the surface of tooth enamel is clinically found damaged, the deep tissues of the tooth have been damaged in a large range and dental hard tissue defects have been formed. Therefore, in order to prevent undermining caries it is important to effectively detect and dynamically monitor the early demineralization of tooth hard tissue. Early demineralization of dental hard tissues that are discovered early can be treated with mineralization solutions containing calcium, phosphorus and fluorine, thereby remineralizing the early demineralized tooth hard tissues (such as tooth enamel and cementum), restoring the hardness of the tooth hard tissues, and terminating or eliminating early caries. Such treatment is reversible and may prevent further damage of dental hard tissue. Once caries cause substantial tooth hard tissue defects, restoration materials are needed to restore the tooth morphology.

At present, the detection methods and diagnosis basis of dental caries are mainly clinical examination combined with X-ray imaging. However, the internal demineralization of the tooth hard tissue formed in the early stage of the disease can hardly be confirmed by clinical examination such as visual examination and explorer detection because there are often no obvious signs on the surface of the tooth. X-ray imaging technology can not only cause radioactive contamination, but also can hardly obtain clear X-ray images of the early demineralization of tooth enamel, thereby severely limiting the accurate diagnosis of early caries.

SUMMARY OF THE INVENTION

In order to solve the above problems, the present application aims to design a visual imaging system based on PS-OCT for quantitative evaluation of early dental caries and non-carious dental hard tissue demineralization in the oral cavity. The visual imaging system can be used for effectively monitoring the dental hard tissues with early demineralization in the oral cavity, accurately and quantitatively evaluating the lesion range and depth of early dental caries in the oral cavity, and thus providing a reliable basis for the diagnosis and treatment by clinicians.

The technical solution adopted by the present application is as following.

In a first aspect, the present application provides a visual imaging device based on PS-OCT for early demineralization and caries of dental hard tissues, comprising a laser light source for emitting a laser light, a coupler for receiving and dividing the laser light emitted by the laser light source into a reference laser light and a detection laser light;

a reference optical path, configured to let the reference laser light pass through a polarizer, an optical grating, and an optical path length adjuster to reach a reflecting mirror for reflecting the reference laser light, and the reference laser light reflected by the reflecting mirror backtrack to the coupler;

a detection optical path, configured to let the detection laser light pass through a scanning galvanometer comprising a galvanometer in X-axis direction and a galvanometer in Y-axis direction, and the detection laser light through the scanning galvanometer pass through a convex lens to reach a tooth to be detected in vivo, and the detection laser light reflected by the tooth backtrack to the coupler;

wherein the reference laser light backtracking to the coupler and the detection laser light backtracking to the coupler are coupled and then passed through a transmission grating and a convex lens to input as an optical signal into a linear CCD detector for converting the optical signal into an electrical signal which is then input to a computer acquisition and imaging system and collected by a built-in capture card; and the computer acquisition and imaging system is configured to perform a three-dimensional reconstruction of an image and perform cross-section analysis; and wherein the computer acquisition and imaging system is connected to the scanning galvanometer to control a vibration of the scanning galvanometer.

Preferably, the detection optical path is provided with an inspection handle, inside which the scanning galvanometer and the convex lens in the detection optical path are installed, and wherein the inspection handle is provided with a probe, on top of the probe is provided with a detection window, and one side of the detection window is provided with a reflecting mirror for reflecting a laser light.

Preferably, the computer acquisition and imaging system is further connected with a parameter adjustment display, a parameter adjustment panel and a control foot pedal.

In a second aspect, the present application provides a method of using the visual imaging device according to claim 1, wherein the method comprises steps of:
1) placing a head of an inspection handle on a surface of tooth to be detected in the oral cavity of a subject, and stepping on a foot pedal to start the inspection;
2) passing a polarized diode laser light emitted by a laser light source through an optical fiber coupler to generate a reference laser light and a detection laser light which enter a reference optical path and a detection optical path respectively;
3) passing the reference laser light which enters the reference optical path through a polarizer to generate a polarized reference laser light, passing the polarized reference laser light successively through an optical fiber coupler, an optical grating and an optical path length adjuster to reach a reflecting mirror which reflects back the laser light to form a reference arm beam;
4) passing the detection laser light which enters the detection optical path successively through an optical fiber coupler, a scanning galvanometer and a convex lens to reach the surface of tooth to be detected of the subject, and returning backing the detection laser light reflected by the tooth through the detection optical path to form a detection arm beam;
5) coupling the reference arm beam and the detection arm beam through an optical fiber coupler to generate a coupled light, passing the coupled light through a transmission grating to form scattered lights, converging the scattered lights through a convex lens to form parallel lights, inputting the parallel lights as an optical signal into a linear CCD detector for converting the optical signal into an electrical signal; and
6) inputting the electrical signal into a computer acquisition and imaging system, collecting information by a built-in capture card, performing graphic processing and displaying a three-dimensional reconstructed image and two-dimensional cross-sectional image on a screen for a doctor to inspect.

The present application has the following beneficial effects:

The visual imaging device based on PS-OCT for early demineralization and caries of dental hard tissues designed by the present application can be used for performing PS-OCT imaging detection of the dental hard tissue surface in the oral cavity of a subject. The computer acquisition and imaging system automatically performs two-dimensional cross-section imaging and three-dimensional reconstruction imaging of the image, thereby completing a three-dimensional quantitative evaluation. The present application provides a new method for detecting early demineralization of dental hard tissue with high resolution.

REFERENCE NUMBERS

01—optical path length adjuster; 02—reflecting mirror; 03—optical grating; 04—optical fiber coupler; 05—polarizer; 06—laser light source; 07—optical fiber coupler; 08—coupler; 09—optical fiber coupler; 10—transmission grating; 11—convex lens; 12—linear CCD detector; 13—computer acquisition and imaging system; 14—optical fiber coupler; 15—scanning galvanometer; 16—convex lens; 17—detection sample; 18—scanning galvanometer; 19—optical fiber coupler; 20—convex lens; 21—inspection handle and a probe; 22—reflecting mirror; 23—probe detection window; 24—detection sample; 25—computer control system; 26—parameter adjustment display; 27—parameter adjustment panel; 28—oral inspection handle and a probe; 29—handle bracket; 30—foot pedal.

DETAILED DESCRIPTION OF EMBODIMENTS

Figure 1:
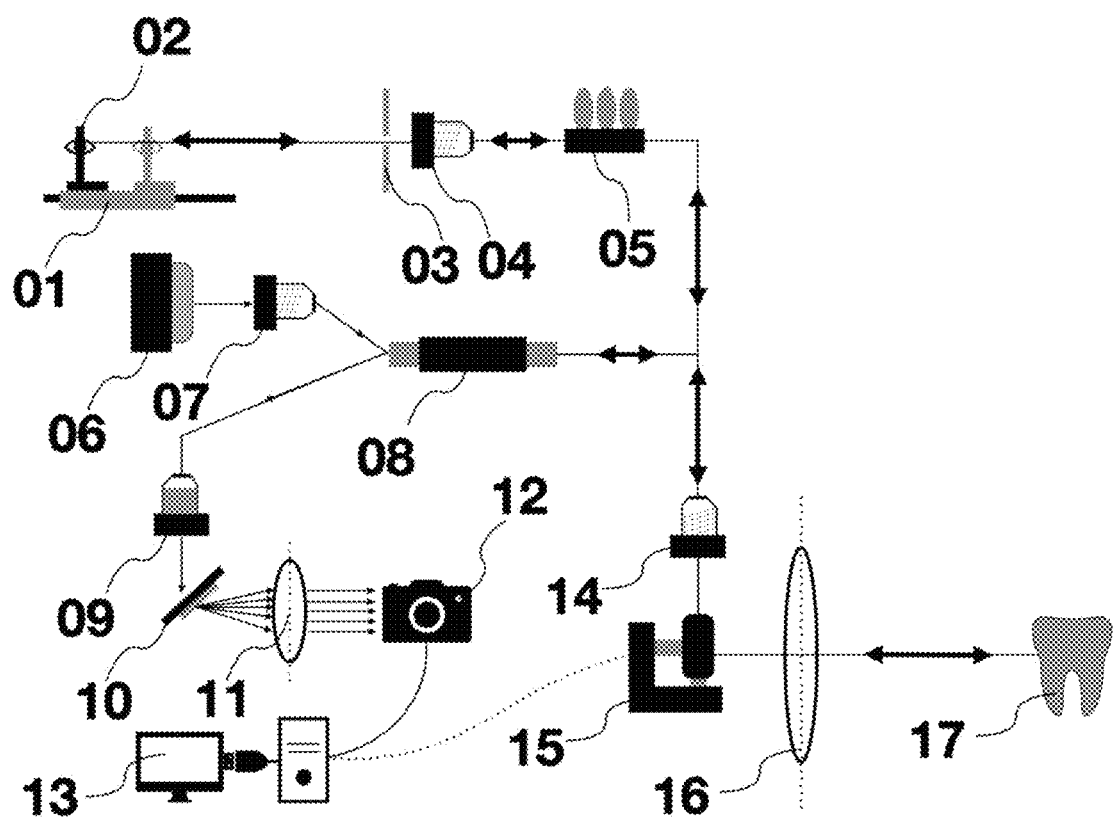
FIG. 1 is diagram showing a design of the optical path of a visual imaging device based on PS-OCT.

As shown in FIG. 1, a visual imaging device based on PS-OCT comprises a diode laser light source, a reference arm, a sample arm and a spectrometer. A polarized diode laser light from a laser light source 06 is coupled by passing through an optical fiber coupler 07, input into a coupler 08 and then input into the reference arm and the sample arm respectively. The light beam which enters the reference arm is polarized by passing through a polarizer 05 to obtain a polarized light. The polarized light is adjusted by passing through an optical fiber coupler 04 and an optical grating 03, then passed through an optical path length adjuster 01 and reflected by a reflecting mirror 02 to form a reference arm beam. The light beam which enters the sample arm passes through an optical fiber coupler 14 to reach a scanning galvanometer 15. The scanning galvanometer 15 includes a galvanometer in X-axis direction and a galvanometer in Y-axis direction. The vibration of the scanning galvanometer 15 is connected to a computer acquisition and imaging system 13. The light beam passes through the scanning galvanometer 15 and then passes through a convex lens 16 to reach a detection sample 17, and the light reflected by the detection sample backtracks through the sample arm. The light beam backtracking from the reference arm and light beam backtracking from the sample arm are coupled through the coupler 08 to form a coupled light which then enters a spectrometer. The coupled light enters a transmission grating 10 to form scattered lights which are then converted to form parallel lights by passing through a convex lens 11. The parallel lights as an optical signal are input into a linear CCD detector 12 for converting the optical signal into an electrical signal. The electric signal is input into a computer acquisition and imaging system 13 and collected by a built-in capture card. The computer acquisition and imaging system 13 is also connected to the scanning galvanometer 15 to control the vibration of the galvanometer. The computer acquisition and imaging system 13 integrates a high-performance graphics card which can perform a three-dimensional image reconstruction and two-dimensional cross-section image analysis.

Figure 2:
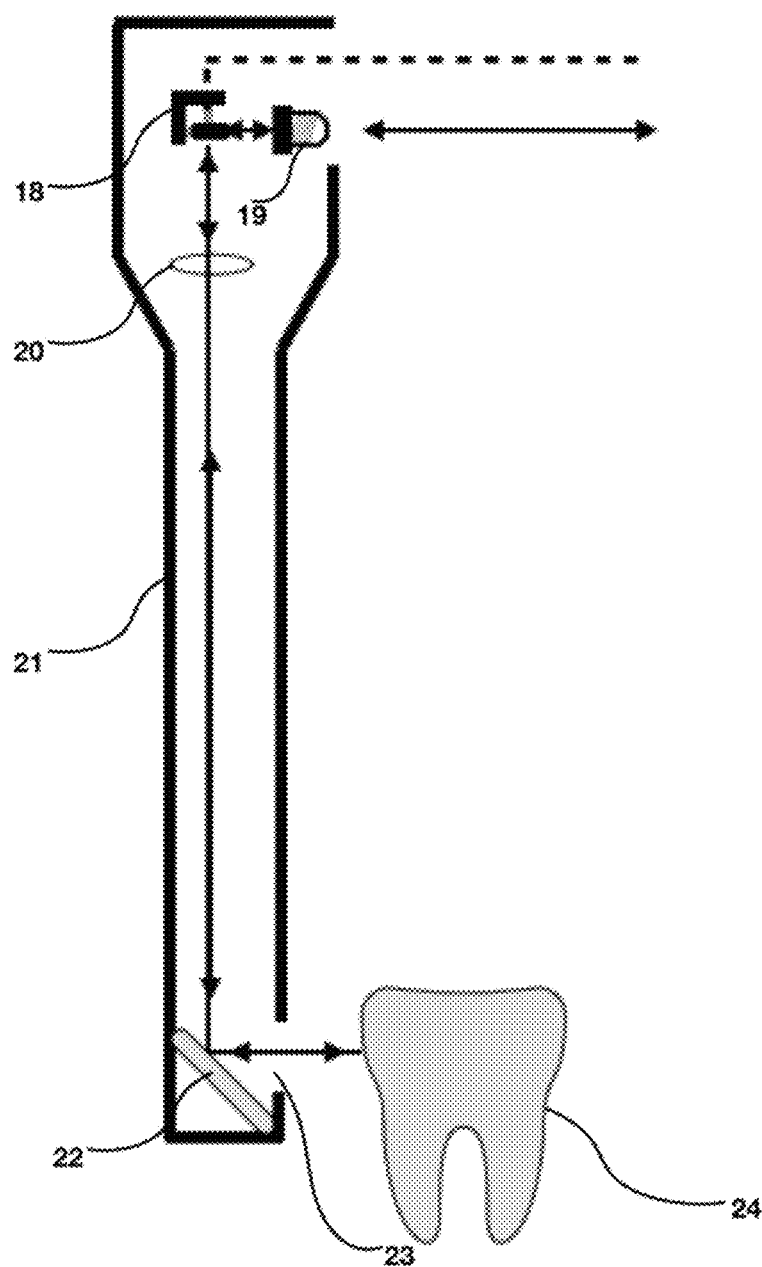
FIG. 2 is a diagram showing a design of an inspection handle.

As shown in FIG. 2, an oral inspection handle and a probe 21 are designed to mainly include a built-in optical fiber coupler 19, a scanning galvanometer 18, a convex lens 20 and a reflecting mirror 22. A polarized light emitting from a polarized light generator enters the inspection handle through the transmission along the optical fiber. The polarized light passes through the fiber coupler to reach the scanning galvanometer comprising a galvanometer in X-axis direction and a galvanometer in Y-axis direction. The galvanometer in X-axis direction and the galvanometer in Y-axis direction are controlled by the computer acquisition and imaging system to perform vibration. The light passing through the scanning galvanometer passes through the convex lens to reach the reflecting mirror. The light reflected by the reflecting mirror passes through a probe detection window 23 to reach a detection sample 24. Then the lights reflected by the detection sample are collected and backtrack to the spectrometer.

Figure 3:
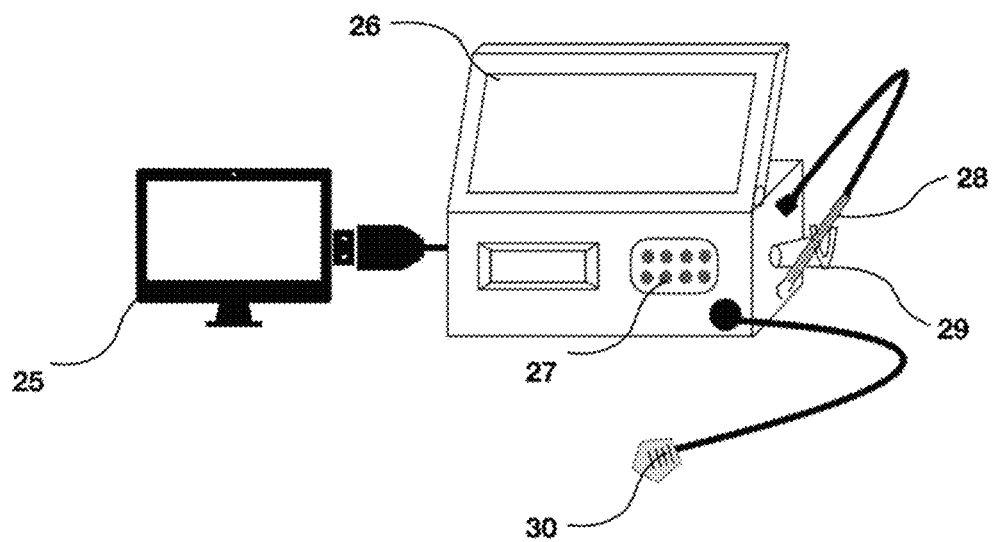
FIG. 3 shows an overall design of the device.

As shown in FIG. 3, an overall design of the device includes a computer control system 25, an imaging device based on PS-OCT, a parameter adjustment display 26, a parameter adjustment panel 27, an optical fiber transmission system, a foot pedal 30, an oral inspection handle and a probe 28. The computer control system has a built-in capture card and software that can adjust detection parameters, perform three-dimensional reconstruction of the detection image, and directly perform measurement and evaluation of the depth and range of demineralization. The imaging device based on PS-OCT integrates a diode laser light source, a reference arm of the detection system based on PS-OCT and a spectrometer. The optical fiber transmission system connects the imaging device based on PS-OCT with the oral inspection handle and probe to transmit optical signals. The oral inspection handle is suitable for being placed in the oral cavity of a subject for collecting optical signals and transmitting the optical signals back to the spectrometer via optical fibers. The doctor controls the starting and stopping of the inspection by controlling the foot pedal 30.

A method of using the imaging device based on PS-OCT in the present application comprises steps of:
1. A subject lies on the dental chair, and the position of the subject is adjusted and the chair light is checked;
2. The switch of PS-OCT device is turned on, a head of the intraoral inspection handle is placed on a surface of tooth to be detected in the oral cavity of the subject, and the doctor steps on a foot pedal to start the inspection;
3. A polarized diode laser light is emitted by the laser light source and passes through the optical fiber coupler to generate the reference laser light and the detection laser light which enter the reference arm and the sample arm respectively;
4. The reference laser light which enters the reference arm firstly passes through a polarizer to generate a polarized reference laser light, and the polarized reference laser light passes successively through an optical fiber coupler, an optical grating and an optical path length adjuster to reach a reflecting mirror which reflects back the laser light to form a reference arm beam;
5. The sample laser light which enters the sample arm passes successively through an optical fiber coupler, a scanning galvanometer and a convex lens to reach the surface of tooth to be detected of the subject, and the sample laser light reflected by the tooth returns back through the sample arm to form a sample arm beam; wherein the vibration of the scanning galvanometer is connected with the computer control system;
6. The reference arm beam and the sample arm beam are coupled through an optical fiber coupler to generate a coupled light, then the coupled light passes through a transmission grating to form scattered lights, and the scattered lights are converged through a lens to form parallel lights, and the parallel lights are input as an optical signal into a linear CCD detector for converting the optical signal into an electrical signal; and
7. The electrical signal is input into a computer acquisition and imaging system and collected by a built-in capture card, then the graphic processing is performed by a high performance graphics card and a three-dimensional reconstructed image and two-dimensional cross-section image are displayed on a screen for a doctor to inspect.

The above-described examples are only preferred embodiments of the present application, and are not intended to limit the present application. It should be understood that the present application is not limited to the form disclosed herein. The modifications or variations made by those skilled in the art should fall within the protection scope of the appended claims of the present application, as long as they do not depart from the spirit and scope of the present application.

What is claimed is:

1. A method of using a visual imaging device based on PS-OCT for early demineralization and caries of dental hard tissues, wherein the visual imaging device includes a laser light source for emitting a laser light; a coupler for receiving and dividing the laser light emitted by the laser light source into a reference laser light and a detection laser light; a reference optical path configured to let the reference laser light pass through a polarizer, an optical grating, and an optical path length adjuster to reach a reflecting mirror for reflecting the reference laser light and the reference laser light reflected by the reflecting mirror backtrack to the coupler; a detection optical path configured to let the detection laser light pass through a scanning galvanometer including a galvanometer in X-axis direction and a galvanometer in Y-axis direction, and the detection laser light through the scanning galvanometer pass through a convex lens to reach a tooth to be detected in vivo, and the detection laser light reflected by the tooth backtrack to the coupler; wherein the detection optical path is provided with an inspection handle, inside which the scanning galvanometer and the convex lens in the detection optical path are installed, and wherein the inspection handle is provided with a probe, on top of the probe is provided with a detection window, and one side of the detection window is provided with a reflecting mirror for reflecting a laser light, wherein the reference laser light backtracking to the coupler and the detection laser light backtracking to the coupler are coupled and then passed through a transmission grating and a convex lens to input as an optical signal into a linear CCD detector for converting the optical signal into an electrical signal which is then input to a computer acquisition and imaging system and collected by a built-in capture card; wherein the computer acquisition and imaging system is configured to perform a three-dimensional reconstruction of an image and perform cross-section analysis; and wherein the computer acquisition and imaging system is connected to the scanning galvanometer to control a vibration of the scanning galvanometer; and wherein the computer acquisition and imaging system is further connected with a parameter adjustment display, a parameter adjustment panel and a control foot pedal, wherein the method comprises steps of:

(1) placing a head of an inspection handle on a surface of tooth to be detected in the oral cavity of a subject, and stepping on a foot pedal to start the inspection;

(2) passing a polarized diode laser light emitted by a laser light source through an optical fiber coupler to generate a reference laser light and a detection laser light which enter a reference optical path and a detection optical path respectively;

(3) passing the reference laser light which enters the reference optical path through a polarizer to generate a polarized reference laser light, passing the polarized reference laser light successively through an optical fiber coupler, an optical grating and an optical path length adjuster to reach a reflecting mirror which reflects back the laser light to form a reference arm beam;

(4) passing the detection laser light which enters the detection optical path successively through an optical fiber coupler, a scanning galvanometer and a convex lens to reach the surface of tooth to be detected of the subject, and returning backing the detection laser light reflected by the tooth through the detection optical path to form a detection arm beam;

(5) coupling the reference arm beam and the detection arm beam through an optical fiber coupler to generate a coupled light, passing the coupled light through a transmission grating to form scattered lights, converging the scattered lights through a convex lens to form parallel lights, inputting the parallel lights as an optical signal into a linear CCD detector for converting the optical signal into an electrical signal; and (6) inputting the electrical signal into a computer acquisition and imaging system, collecting information by a built-in capture card, performing graphic processing and displaying a three-dimensional reconstructed image and two-dimensional cross-section image on a screen for a doctor to inspect.

\* \* \* \* \*